United States Patent [19]

Sones

[11] Patent Number: 4,987,898

[45] Date of Patent: Jan. 29, 1991

[54] METHOD AND DEVICE FOR THE NON-INVASIVE MEASUREMENT OF PRESSURE

[75] Inventor: William Sones, New York, N.Y.

[73] Assignee: Noninvasive Medical Incorporated, Hackensack, N.J.

[21] Appl. No.: 297,308

[22] Filed: Jan. 17, 1989

[51] Int. Cl.⁵ .............................................. A61B 3/16
[52] U.S. Cl. .................................................. 128/645
[58] Field of Search ............... 128/645, 646, 652, 675, 128/676, 748; 73/715, 723, 725–727, 751, 753

[56] References Cited

U.S. PATENT DOCUMENTS

| | | | |
|---|---|---|---|
| 3,677,074 | 7/1972 | Murr | 128/645 |
| 4,398,427 | 8/1983 | Pan | 73/726 |
| 4,600,855 | 7/1986 | Strachan | 128/675 |
| 4,640,295 | 2/1987 | Isaacson | 128/748 |
| 4,747,296 | 5/1988 | Feldon et al. | 128/652 |

FOREIGN PATENT DOCUMENTS

146907  3/1961  U.S.S.R. ............................ 128/652

Primary Examiner—William E. Kamm

[57] ABSTRACT

An improved, non-invasive pressure sensing method and device is provided which allows for the measurement of pressure in a vessel having flexible walls or otherwise provided with an external elastic membrane. The disclosed method and device provides for the application of a coplanar array of pressure sensors or transducers against the elastic vessel wall, the internal pressure of the vessel being measured at a point at which at least three of the transducers, arranged in a triangular configuration, measure the same pressure.

17 Claims, 7 Drawing Sheets

METHOD AND DEVICE FOR THE NON-INVASIVE MEASUREMENT OF PRESSURE

FIELD AND BACKGROUND OF THE INVENTION

The present invention relates generally to pressure sensing probes and more particularly to a non-invasive pressure sensing method and apparatus for measuring internal pressure of a vessel or cavity having at least a portion of the one wall made up of an elastic membrane or in which an elastic membrane can be fitted.

The use of non-invasive measurement has received considerable attention in recent years. In particular, in the fields of physiology and medicine, this method has seen considerable development and utilization in cardiology, obstetrics and ophthalmology.

While the use of non-invasive pressure measuring devices, or tonometers, for applications such as measuring ocular pressure to determine the existence of glaucoma and measuring intracranial pressure of newborns, is well known, the existing methods and apparatus utilized are inaccurate and, for some applications, impractical.

One known method of non-invasive tonometer predominantly used in medical applications contemplated for the present invention utilizes a single pressure transducer and coplanar "guard ring" developed in the late 1950's. Such a device is discussed in Mackay, R.S. and Marg E., "Fast Automatic Ocular Pressure Measurement based on exact theory". IRE Trans. Med. Electronics, ME-7, 61–67, (1960) and Smyth, C.N. "The Guard-Ring Tocodynamometer: Absolute Measurement of Intra-amniotic Pressure by a New Instrument," J. Obstetrics and Gynecology, 64, 59–66 (1957).

Figure 1:
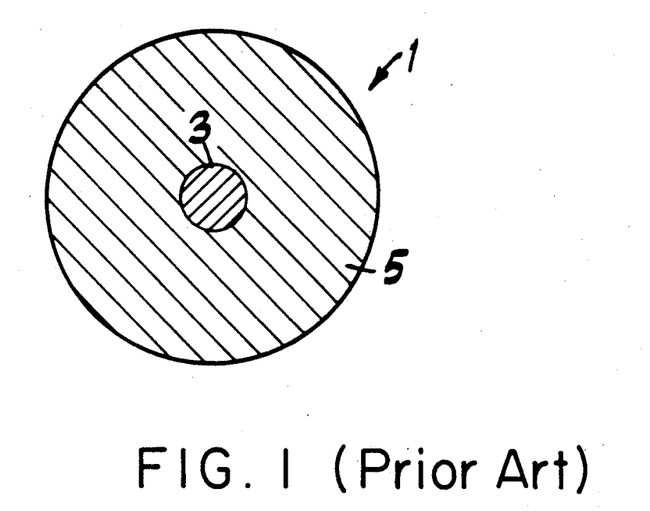
FIG. 1 is a graphic depiction of a prior art "guard ring" tonometer.
Figure 2:
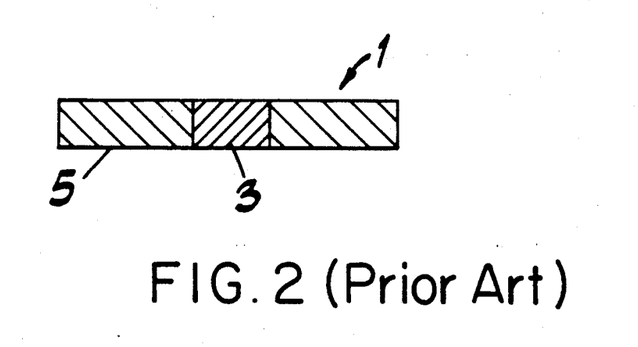
FIG. 2 is a side perspective of the "guard ring" tonometer of FIG. 1.

As depicted in FIG. 1 hereto, the prior art guard ring tonometer, 1, consists of a single central force transducer, 3, surrounded by an annular ring, 5. As shown in FIG. 2, the force transducer, 3, is disposed within the annular ring 5 and is coplanar therewith.

Figure 3:
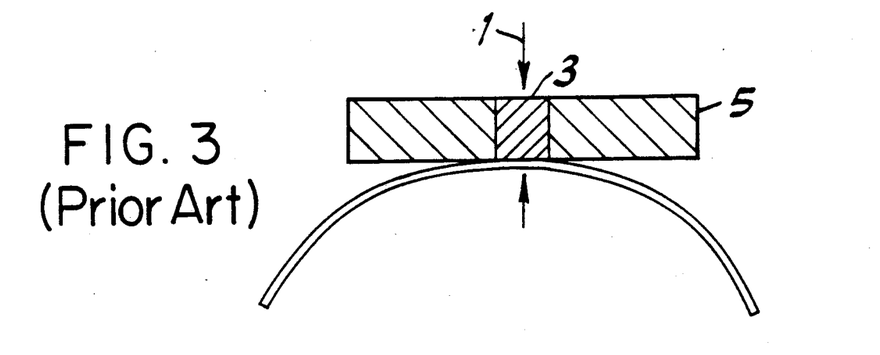
FIGS. 3–5 depict application of the "guard ring" tonometer of FIGS. 1–2 against the pressurized vessel being measured, with application force against the vessel being increased progressively from FIG. 3 to FIG. 5.
Figure 4:
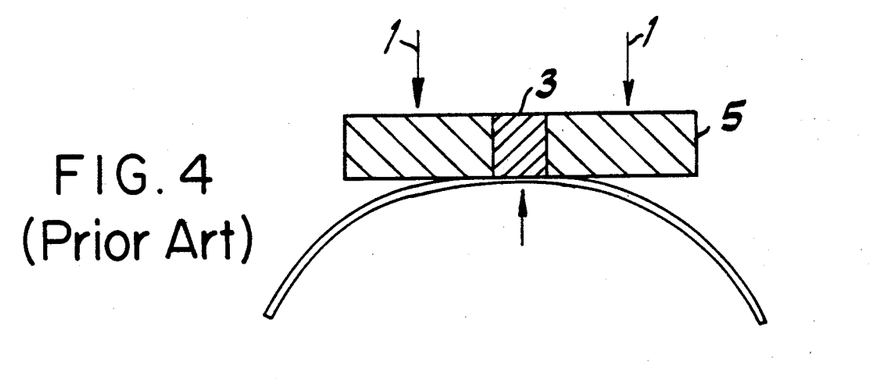
Figure 5:
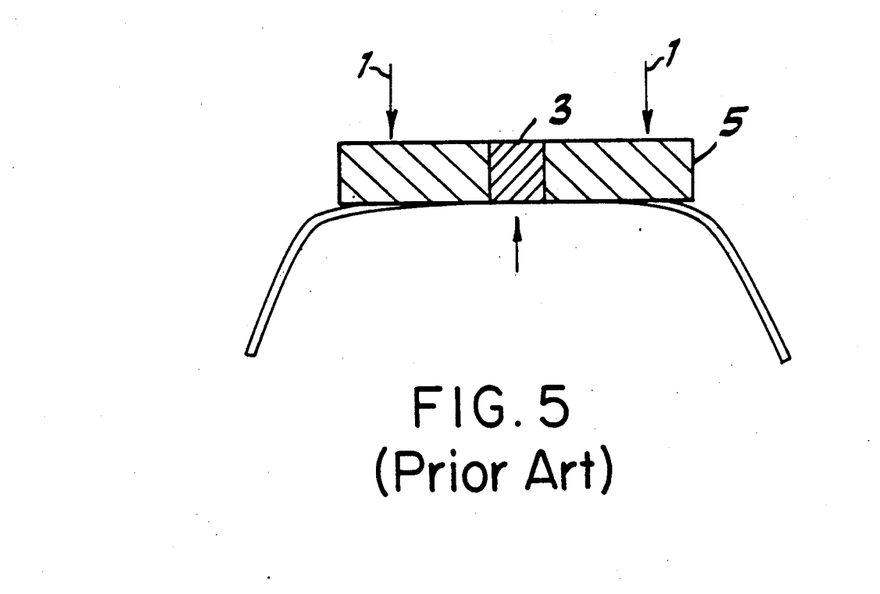

In operation, the guard ring tonometer, 1, is advanced against the surface of a pressurized elastic membrane of the vessel under review, as shown in FIGS. 3–5, causing the pressure sensed by the central transducer, 3, to increase as the tonometer, 1, is advanced and the membrane of the pressurized vessel, contacting the tonometer, 1, is increasingly flattened.

When the membrane just covers the central transducer, 3, [FIG. 4] the sensed pressure is at a maximum value, since the internal pressure of the vessel and the pressure required to bend the membrane will both be measured by the transducer, 3.

As the tonometer, 1, is further advanced toward the vessel, [FIG. 5] the bending force component of the measured pressure is transferred outwardly to the fixed annular ring, 5, causing the measured pressure at the central pressure transducer, 3, to reach a minimum. At this point, the pressure registered by the central transducer, 3, is equal to the pressure internal to the vessel.

In essence, the fixed coplanar annular ring, 5, acts as a "guard ring" to prevent the bending forces from affecting the measurement. As the tonometer, 1, is further advanced, the indicated pressure again increases owing to the increase in pressure caused by the tonometer displacement or invagination of the pressurized membrane.

An alternative way of describing this technique is to note that upon depression of the guard ring, 5, sufficiently to applanate the elastic membrane of the vessel, the radius of the membrane apparent to transducer, 3, becomes essentially infinite. Thus, there is no contribution in the measured pressure due to bending forces, because the effect of any bending force components occurs outside the radius detected by the transducer, 3.

The use of the "guard ring" tonometer, 1, [and all current related methods and devices] as described above, has several difficulties associated with its operation, especially when used for long term, continuous measurements.

For example, it is difficult to determine when to stop advancing the tonometer, even for short, single sample measurements. One may use a readout device to sense the increase, decrease and increase in pressure as described in the use of this device. But it will be difficult to know just when to stop advancing the tonometer. Moreover, if pressure is variable, either due to the vessel itself or because of application force or movement of the tonometer, rapid and accurate adjustments to the tonometer to ensure accurate readings by manual methods based on the increase and decrease of pressure are difficult at best. Also, if the tonometer is attached to the membrane by utilizing a fixturing method, the tonometer may move or come loose after it was properly mounted or the pressure of the vessel may change.

Unless the operator continually moves the tonometer about to determine if it is at the point of minimal pressure, it is thus unclear whether or not the membrane remains properly applanated for accurate pressure measurements. The "guard ring" tonometer method of non-invasive pressure measurement is therefore effective, if at all, for a single measurement sample, taken over a brief period of time.

One attempt to solve this problem, discussed in the Marg reference cited above, was to provide transducers at a given periphery in the guard ring and to measure the pressure upon simultaneous activation of these sensors. This did not, however, ensure against unequal pressure being applied to some of the periphery transducers, thereby resulting in improper pressure readings. This method also fails to provide for anything but single discrete measurements, because movement of the tonometer may continue to activate the peripheral sensors while creating a false increase in the pressure reading due to added application pressure on the guard ring tonometer.

Another known, and more recently developed, method of non-invasive pressure measurement, utilized for intracranial pressure applications, involves a transducer that is slowly forced against the subject membrane by a lead screw. Such a device is described in Majors et al., "Intracranial Pressures Measured with the Coplanar Transducer". Med. Biol. Eng. 10, 724–733 (November 1972). As With the "guard ring" tonometer approach, the accuracy of this method is dependent upon operator skill and experience in observing various pressure readings as the transducer is applied against the subject vessel and selecting the optimum application force for sensing the pressure. This approach also fails to address problems associated with changing conditions invalidating original settings discussed above with reference to the guard ring tonometer.

Many attempts at measuring intracranial and ocular pressure and similar applications have been made by using single pressure transducers, with and without guard rings. In all cases, the difficult problem remains as to when to stop the application of the transducer against the membrane to make a pressure reading that one can call the actual vessel pressure. A related and serious problem is that if one has indeed found the correct application pressure and mounts a transducer against the membrane to make a reading, changing conditions of internal pressure in the vessel or of the means of mounting the transducer to the membrane will invalidate the readings of pressure when the transducer either looses its coplanarity or is actually being applied with too much pressure, thereby recreating bending forces on the membrane and thus increasing the vessel pressure. One survey of just such attempts involved in the measurement of intracranial pressure and confirmation of these problems associated with the simple application of a single transducer to a membrane can be found in, "Clinics in Perinatology/Noninvasive Neonatal Diagnosis," February 1985, edited by Alistair G.S. Philip, M.D., published by W.B. Saunders Co.

No general provision exists in the known non-invasive pressure sensing methods and devices for simple precise control of the application force to ensure accurate pressure readings. While the known sensing devices provide for instantaneous, discrete measurements, the accuracy of these measurements and the possibility of continued monitoring of the tonometer is subject to operator skill and experience, as well as the changes and pressure of the vessel under investigation and movement of the tonometer itself. It is, therefore, of substantial interest for medical and similar applications involving the need to measure the pressure of a vessel provided with a flexible, external membrane to provide a method and apparatus to simplify and improve the precision of pressure measurement on both an instantaneous and continual basis, and that this method and apparatus be adapted for ease of adjustment where changes and conditions related to the vessel pressure and application of the pressure transducer(s) vary.

SUMMARY OF THE INVENTION

It is, accordingly, an object of the present invention to provide a non-invasive method and apparatus to simply and effectively determine the pressure of a vessel provided with an external, elastic membrane.

It is a further object of the present invention to provide a non-invasive method and apparatus by which changes in pressure within the vessel being tested may be readily detected and measured.

It is still a further object of the present invention to provide a method and apparatus which may be readily adjusted to correct for displacements of the pressure measuring apparatus.

It is still a further object of the present invention to provide a method and apparatus utilizing an array of coplanar sensors or transducers to determine the pressure of a vessel having an external, elastic membrane.

In accordance with the present invention, a pressure sensor array comprising at least three individual coplanar pressure transducers is applied against the external, elastic membrane of a subject vessel. Means are provided to convey the pressure readings from each of these pressure transducers to an instrument for signal processing. Comparison of pressure readings of at least three coplanar pressure transducers arranged in triangular configuration is utilized by the tonometer device to indicate when the elastic membrane is sufficiently applanated to take accurate pressure readings, being a point at which equality of the pressure readings is achieved The value of the pressure detected by any one of these three pressure transducers is then measured as the pressure internal to the pressurized vessel.

In a preferred embodiment of the present invention, a fourth pressure transducer is placed in the center of the coplanar triangular transducer array. This arrangement requires that all four transducers provide equal readings when pressed against the elastic membrane to ensure sufficient applanation of the membrane for accurate pressure measurement. The practical advantage of this last arrangement is that if the center pressure sensor is read as the internal value of the pressure in the vessel, then any edge effects that might interfere with readings from one of the three transducers at the vertices of the triangular array, will be eliminated.

BRIEF DESCRIPTION OF THE DRAWINGS

Other objects and advantageous features of the invention will be apparent in a description of specific embodiments thereof, given by way of example only, to enable one skilled in the art to readily practice the invention which is described hereinafter with reference to the accompanying drawings in which like numerals are intended to refer to like elements.

DESCRIPTION OF SPECIFIC EMBODIMENT

Figure 6:
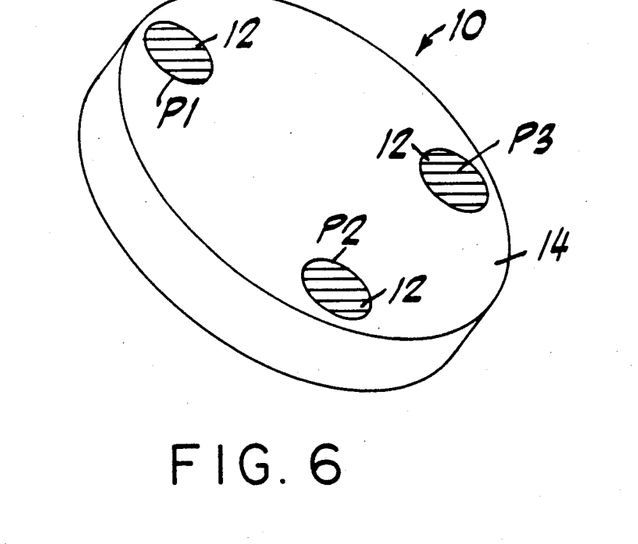
FIG. 6 is a schematic view of a sensor surface of a preferred embodiment of the present invention.

In accordance with the subject invention, a pressure sensor array, denoted generally as 10 in FIG. 6, is provided, including at least three individual pressure transducers, 12, mounted at each of the vertices, P1, P2 and P3 of a triangle along a planar surface, 14, such that the face of each pressure transducer, 12, is coplanar with the surface, 14. This sensor array, 10, is then mounted to a probe, 20, [FIG. 7] which may then be applied to the subject vessel whose internal pressure is to be determined.

Figure 7:
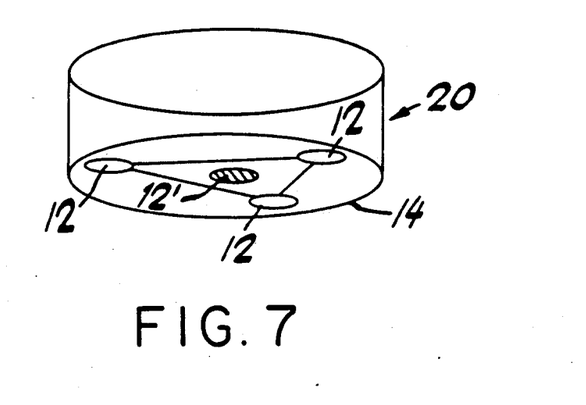
FIG. 7 is a schematic view of the pressure sensing plate utilized in a preferred embodiment of the present invention, showing the triangular array of pressure transducers disposed in a coplanar surface of the plate and a fourth pressure transducer centrally disposed within the triangular array of pressure transducers according to an alternative embodiment of the present invention.

The probe may be of any suitable configuration determined by ease of handling and the configuration of the vessel to be tested, provided the probe includes a rigid, flat supporting surface area and is made of sufficiently durable construction to maintain the pressure of the sensing array, 10, in planar configuration as it is being applied against the vessel surface.

Electrical or other suitable means are provided to convey the pressure readings of the transducers to an instrument for signal processing. The pressure transducers can utilize optical, pneumatic, electrical or any other transduction method.

Figure 8:
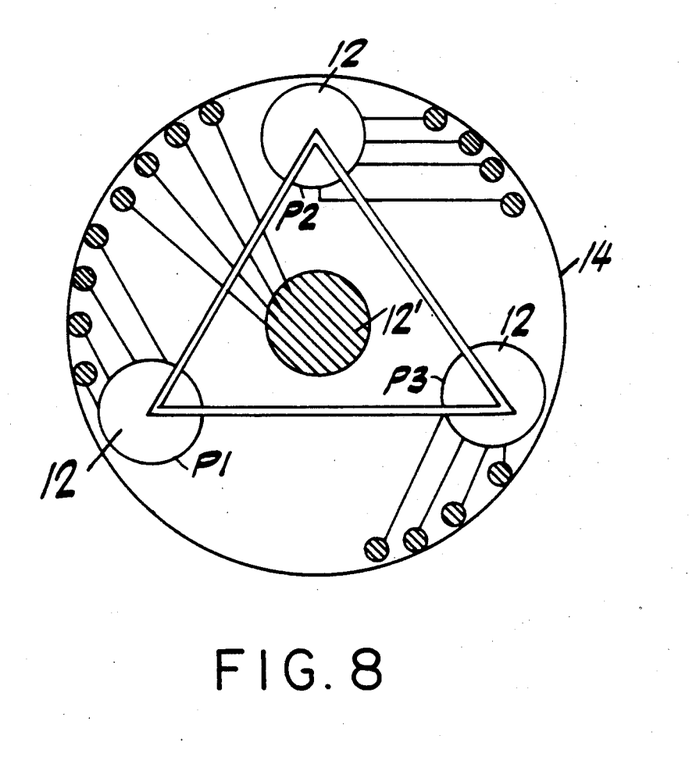
FIG. 8 is a schematic view of the planar surface of the pressure sensing plate of FIG. 7 further depicting the excitation input and signal output to and from the coplanar transducers on the plate.
Figure 9A:
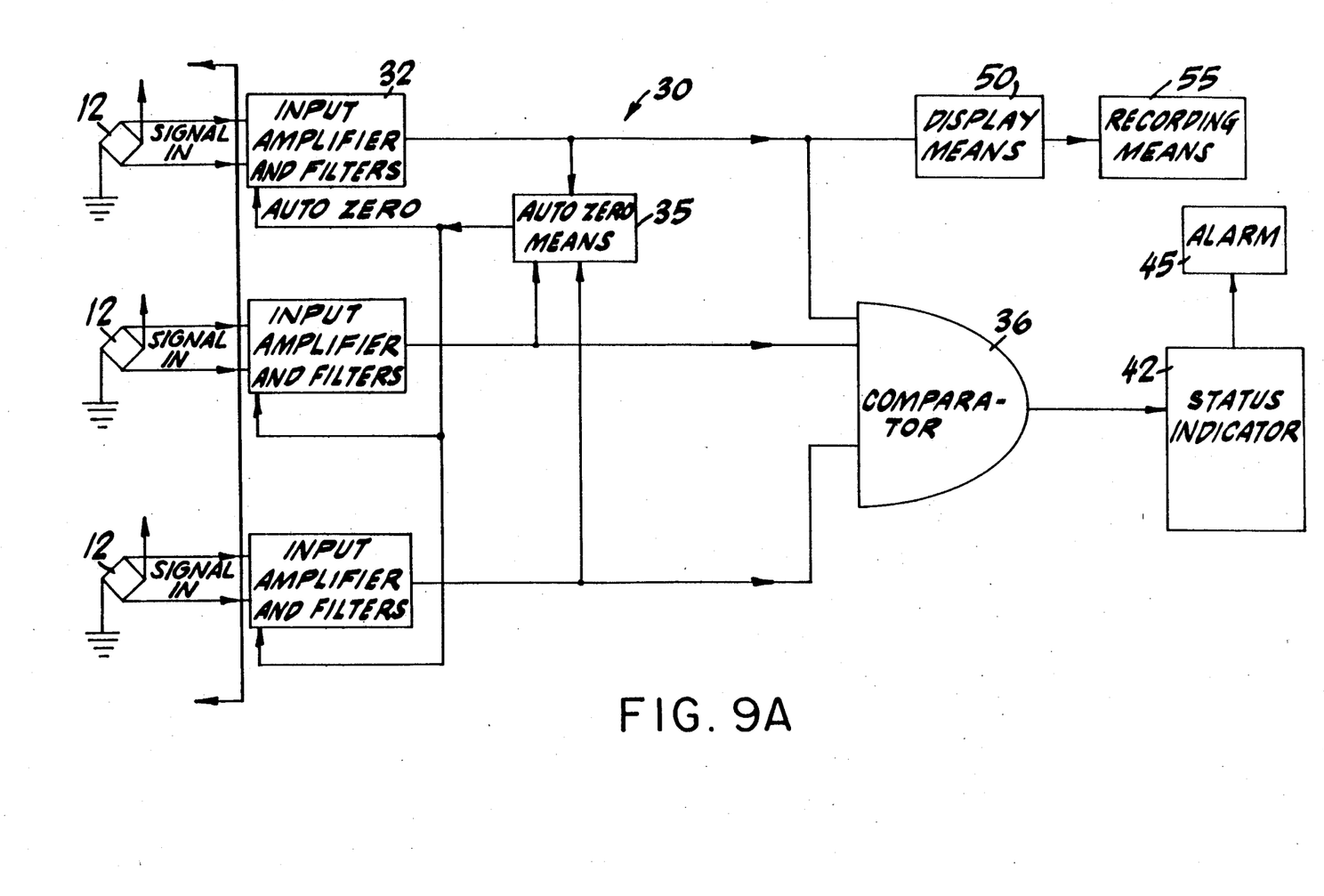
FIG. 9A is a schematic view of the comparator circuitry for determining coincidence of pressure signals across the coplanar triangular, three sensor array.
Figure 9B:
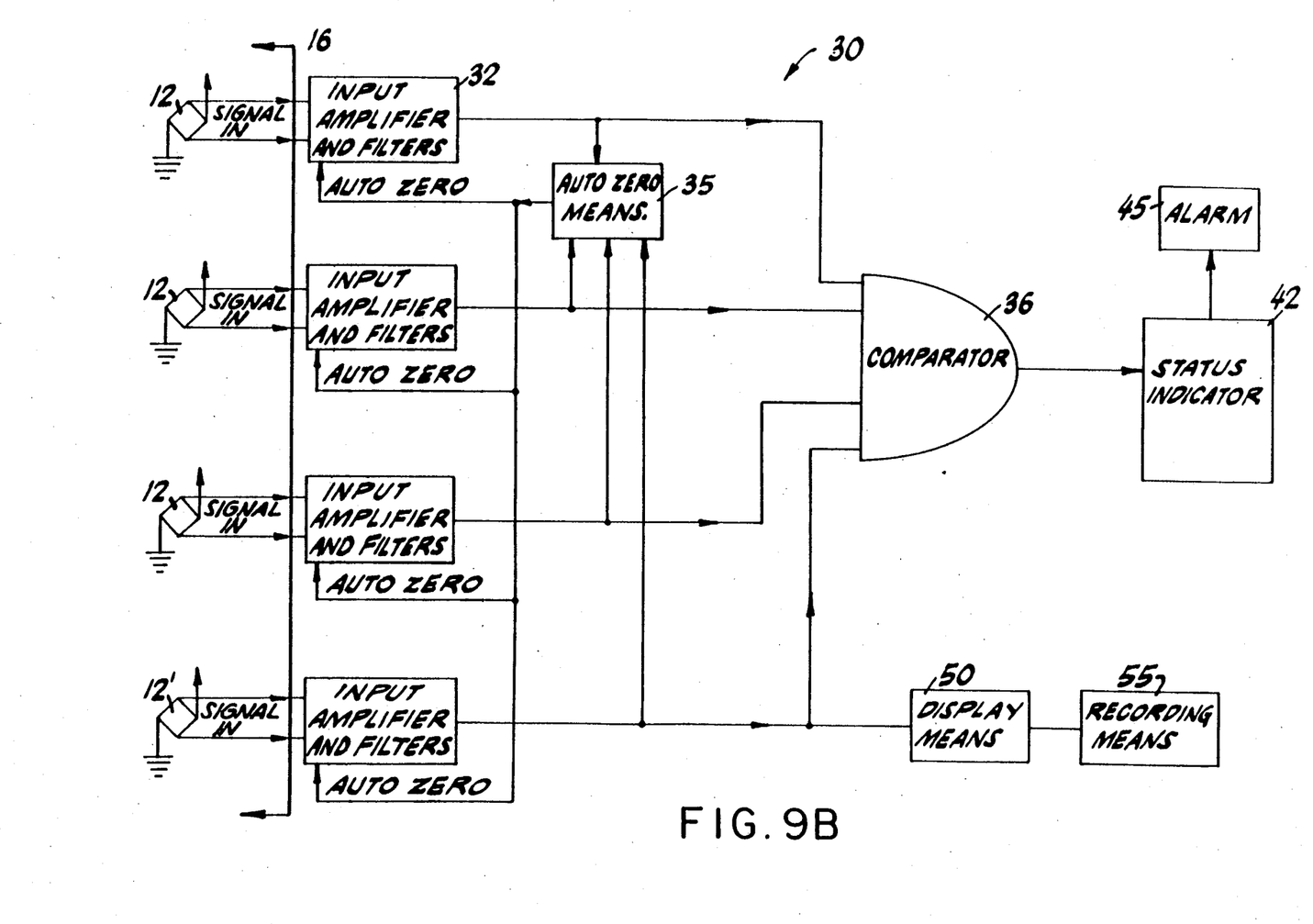
FIG. 9B is a schematic view of the comparative circuitry of FIG. 9A utilizing an additional sensor, centrally disposed within the coplanar triangular sensor array of FIG. 9A, for measuring pressure.

In one preferred embodiment of the present invention, a pressure sensing array, 10, employing four electrical pressure Wheatstone bridge type transducers, 12, and 12', is utilized, as depicted in FIG. 8. Three of the pressure transducers, 12, are mounted in a coplanar manner on the planar surface, 14, at the vertices, P1, P2 and P3, of a triangle. The fourth transducer, 12', is mounted on the surface, 14, and coplanar therewith and is disposed in the center of the triangle formed by transducers, 12. The pressure signals generated by each transducer, 12 and 12', are conveyed via an electrical sensor cable, 16, to a signal processor, 30, depicted in FIG. 9.

Figure 10:
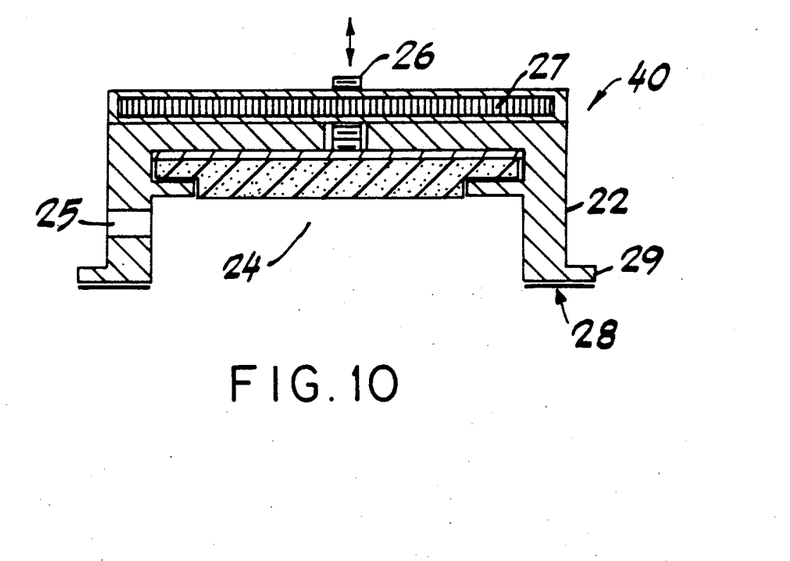
FIG. 10 is a side view, partly in cross section, of an applanation transducer fixturing device incorporating the coplanar assembly of pressure transducers according to a preferred embodiment of the present invention.

The transducer array, 10, may be held against the subject vessel with a doughnut shaped paper disc that has adhesive applied to both sides or by a probe, 20, as discussed above. In one embodiment of the present invention, shown in FIG. 10, the array, 10, is held to the subject vessel within a transducer fixing device, depicted generally as 40 in FIG. 10, having a housing, 22, in which a hole, 24, is made for the sensor array, 10, to be placed. A lead screw, 26, can then be applied through the other side of the housing, 22, to push the sensor array, 10, a controlled distance against the vessel wall. The housing, 22, can then be affixed to the vessel wall with double sided adhesive discs, 28, applied to the footings, 29, of the housing, 22. The housing, 22, may be provided with a channel, 25, through which the sensor cable may be attached to a signal processor, 30.

In a preferred embodiment of the present invention, the signal processor, 30, depicted schematically in FIG. 9, consists of pressure preamplifiers, 32, that filter and amplify the pressure signals from transducers 12. In the embodiment signal processor, 30, depicted in FIG. 9, an arrangement of four preamplifiers, 32, are shown corresponding to the three transducers, 12, affixed in a triangular coplanar arrangement on the tonometer surface, 14, and a fourth transducer, 12', affixed to the surface at the center of the triangle. The preamplifiers, 32, make available a mean or average pressure signal for each sensor, 12 and 12', of the array, 10. The signal processor, 30, also provides an automatic zero circuit, 35, for "zeroing" each individual pressure sensor, 12 and 12'. This is because pressure transducers normally have some signal output or residual imbalance, even with no pressure applied to the sensor face. The zeroing circuitry, 35, ensures that this initial imbalance of the pressure sensors, 12 and 12', does not contribute to the measured pressures. The signal processor, 30, further contains a comparator, 36, that compares the pressure signals from all transducers, 12 and 12', simultaneously. The comparator, 36, determines when, during advancement of the sensor array, 10, against the membrane wall, the pressure sensed by all transducers, 12 and 12', is equal. The determination of equality can be made via any other convenient method, including electronic or mechanical means.

Figure 11:
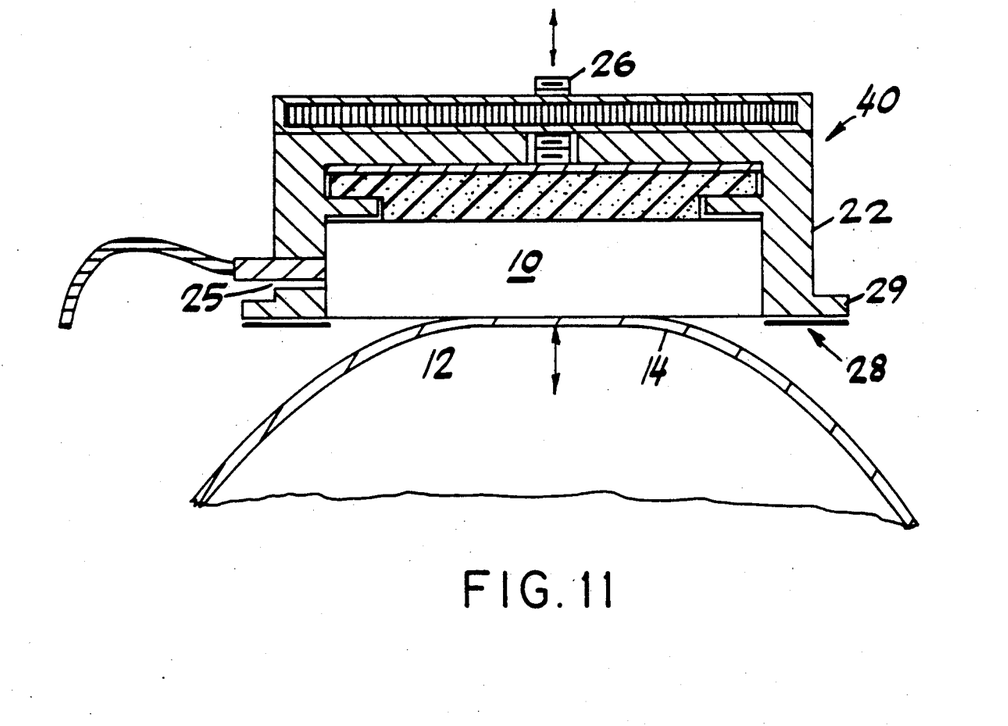
FIG. 11 is a side view of the pressure sensing plate mounted in a fixturing device provided with manual adjustment.

In operation, the sensor array, 10, is held adjacent to the flexible vessel wall, as shown in FIG. 11, without applying pressure to the plate, 14, to which the pressure transducers, 12, are attached. The signal processor zeroing circuit, 35, of FIGS. 9A and 9B, is initiated at this time, causing the outputs of all processing amplifiers, 32, to indicate zero pressure. This may be done by automatic digital means or in a more classic analog electrical circuit. When all pressure sensors, 12, in the array, 10, have been set to zero as above, the array may be secured with tape 28 or otherwise mounted on the flexible vessel wall. Alternatively, a probe, 20, FIG. 7 or transducer fixturing device, 40, may be utilized to advance the array, 10, against the vessel wall.

The sensor array, 10, is then advanced manually or automatically, by lead screw, 26, or similar advancing means against the subject vessel, during which time the signal processor, 30, as depicted in 9A and 9B utilizes comparator circuitry to compare the mean value of all pressure readings generated by each pressure transducer, 12, contacting the vessel wall. At the point at which all transducers, 12, on the array indicate equality of pressure reading with each other, an indicator, 42, either visual or audible will alert the operator that the correct application pressure has been reached. This is then the point at which the surface over which the pressure is being measured is truly applanated. From this point on, signals provided by correlating pressure transducers, 12, or a fourth central pressure transducer, 12', will indicate the true pressure internal to the vessel on which the sensor array, 10, is mounted. Means, 50, may also be provided to display this pressure as a real time pressure curve or as a trend curve of mean pressure. Recording means 55, may also be provided to make paper records and to transmit the signals for further processing by a computer or other data processing means. One may also provide such capabilities as an alarm, 45, to signal the user of values of pressure that are either too high or too low.

As time passes, it is possible that the mounted sensor array, 10, will become unseated from its ideal position of applanation, [all pressure transducers, 12, reading the same pressure]. An alarm, 45, may be provided to detect this out of applanation condition. This alarm, 45, will call the attention of the operator to the machine at which time the operator can reseat the sensor array, 10, until the new in-balance condition is achieved.

Figure 12:
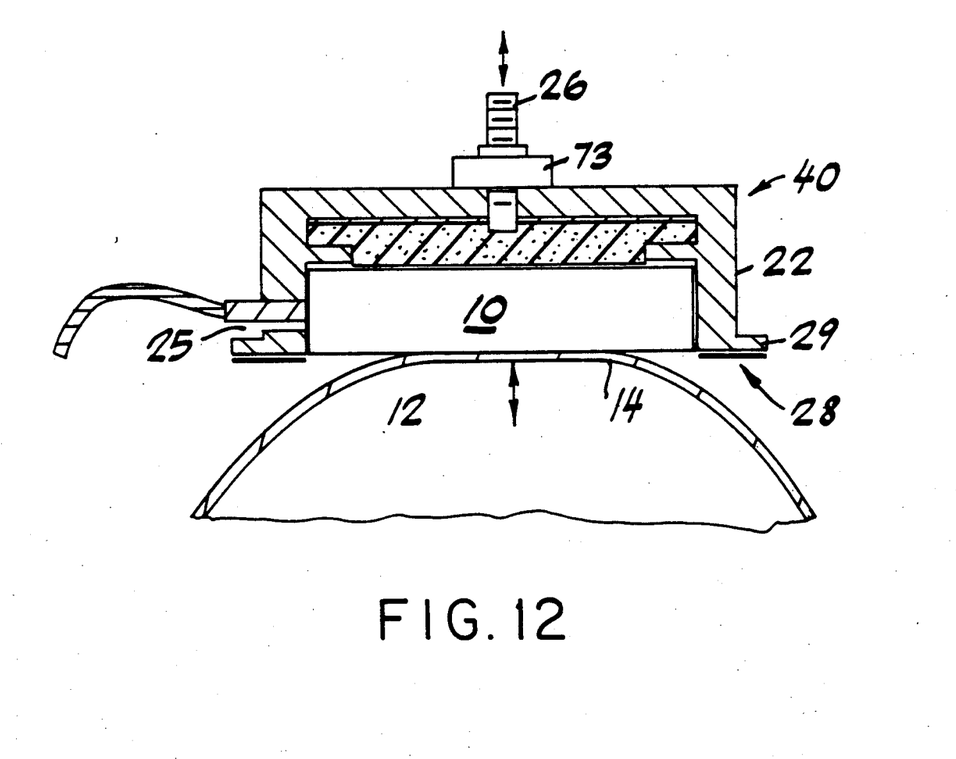
FIG. 12 is a side view of the pressure sensing plate mounted in a fixturing device provided with automatic adjustment.

If a more complete and automatic system is desired, then instead of the operator manually reseating the sensor array, 10, it is possible to have the array, 10, automatically reseated when an out of applanation condition exists. This can be achieved using conventional feedback control system techniques. For example as depicted in FIG. 12, if the fixture, 40, with a lead screw arrangement, 26, is utilized to apply the sensor array, 10, then a motor, 73, attached to the lead screw, 26, could be energized when an out of applanation signal was detected. Upon detection of such a signal, the lead screw, 26, would be backed off until the transducers, 12, read zero applied pressure, at which time, the control system would advance the sensor array, 10, until all transducers, 12, read equal pressure again.

Although the foregoing invention has been described in some detail by way of illustration and example for purposes of clarity of understanding, it will be obvious that certain changes and modifications may be practiced within the scope of the appended claims.

I claim:

1. A method of non-invasive detection of pressure within a vessel having an elastic wall portion, comprising the steps of:
    (a) placing a coplanar triangular array of three pressure transducers into contact with the elastic wall portion;
    (b) monitoring the pressure detected by said transducers;
    (c) advancing said array against said elastic wall portion until the pressure sensed by three monitored transducers is equal; and
    (d) generating a first signal indicating the pressure measured by said transducers when the pressure sensed by said three monitoring transducers is equal.

2. The method of claim 1 further comprising the step of zeroing said pressure transducers prior to said advancing step.

3. The method of claim 1 further comprising the steps of monitoring the pressure of a fourth transducer centrally located within a triangle whose vertices are defined by said three monitored transducers and generating a second signal indicating the pressure within the vessel measured by said fourth transducer.

4. The method of claim 1 further comprising the step of further monitoring said pressure detected by said coplanar sensor array following said generating step and adjusting the position of said pressure sensor array against the elastic wall to maintain said equality of pressure signals.

5. The method of claim 1 further comprising the step of affixing said coplanar array to the elastic wall portion.

6. A device for non-invasive measurement of pressure within a vessel having an elastic wall portion, comprising:
    (a) three pressure transducers arranged in a coplanar triangular array;
    (b) means for bringing said array into contact with the elastic wall portion;
    (c) output means for generating a pressure signal corresponding to the pressure measured by each said pressure transducer;
    (d) comparison means whereby the signals transmitted from the three pressure transducers are compared;
    (e) a signal generating means whereby an indication of signal equality from said three pressure transducers can be displayed or transmitted;
    (f) display means for indicating the pressure measured by said transducers.

7. The device of claim 6, further comprising fixture means for carrying said coplanar array in a predetermined position relative to the vessel.

8. A device for non-invasive measurement of pressure within a vessel having an elastic wall, comprising:
    (a) three pressure transducers arranged in a coplanar triangular array;
    (b) a fourth pressure transducer disposed within said triangular coplanar array;
    (c) means for bringing said array into contact with the elastic wall portion;
    (d) output means for generating a pressure signal corresponding to the pressure measured by each of four said pressure transducers;
    (e) comparison means for determining a condition of equality of said pressure signals from said four pressure transducers;
    (f) signal generating means for indicating the pressure measured by said transducers when the pressure sensed by said four of said monitoring transducers is equal; and
    (g) display means for indicating the pressure measured by the said fourth pressure transducer.

9. The apparatus of claim 8 further comprising signal generating means for generating an equality signal in response to said determination of equality of said pressure 10. The apparatus of claim 8 wherein said coplanar array is carried on a planar surface.

11. The apparatus according to claim 10 wherein said pressure transducers are arranged at the vertices of a triangle on said planar surface.

12. The apparatus of claim 10 further comprising a probe carrying said coplanar array.

13. The apparatus of claim 10 further comprising means for adjusting the position of said planar surface in response to said comparison means to maintain said condition of equality of said pressure signals.

14. The apparatus of claim 8 further comprising means for monitoring said pressure signals from said coplanar transducer array.

15. The apparatus of claim 8 further comprising recording means for recording the pressure within the vessel as indicated by said pressure signals.

16. The apparatus of claim 8 further comprising a fourth transducer disposed centrally to a triangle whose vertices are defined by said three pressure transducers.

17. A device for non-invasively measuring pressure within a vessel having an elastic wall portion, comprising:
    a rigid flat plate;
    three pressure transducers, disposed in a triangular array carried on and coplanar with the surface of said plate;
    means for advancing said array against the surface of said elastic wall portion in a controlled manner;
    output means for generating a pressure signal corresponding to the pressure measured by each said pressure transducer;
    comparison means whereby the signals transmitted from said three pressure transducers are compared;
    control means for repositioning said coplanar array to maintain said condition of equality of said pressure signals;
    means responsive to said control means for repositioning said coplanar array;
    means for displaying and recording the value of any said pressure signal; and
    fixture means for carrying said plate, including housing means for holding said plate in a predetermined position relative to the vessel.

* * * * *